United States Patent [19]

Bonnefous

[11] Patent Number: 4,928,698
[45] Date of Patent: May 29, 1990

[54] DEVICE FOR MEASURING THE SPEED OF MOVING ORGANS AND BLOOD FLOWS BY CORRELATION

[75] Inventor: Odile M. A. Bonnefous, Nogeni Sur Marne, France

[73] Assignee: U.S. Philips Corporation, New York, N.Y.

[21] Appl. No.: 337,024

[22] Filed: Apr. 12, 1989

[30] Foreign Application Priority Data

Apr. 19, 1988 [FR] France ............................... 88 05146

[51] Int. Cl.$^5$ .............................................. A61B 8/06
[52] U.S. Cl. .............................. 128/661.09; 73/861.25
[58] Field of Search ...................... 128/661.07–661.10; 73/861.25

[56] References Cited

U.S. PATENT DOCUMENTS 4,680,739 7/1987 Lannuzel ..................... 128/661.09 X
4,803,990 2/1989 Bonnefous et al. .......... 73/861.25 X Primary Examiner—Francis Jaworski Attorney, Agent, or Firm—William Squire; Thomas A. Briody; Jack E. Haken

[57] ABSTRACT

A device for measuring the speed of moving organs and blood flows, comprising an intercorrelation circuit (100) which supplies on the basis of two successive shifted echographic lines, $2I+1$ correlation function values, and a multiplex/interpolation circuit (200) which supplies, on the basis of the correlation function values, an estimate of the speed and the value of the corresponding correlation peak. In accordance with the invention, the intercorrelation circuit (100) and multiplex/interpolation (200) circuit supply the estimate of the speed and the value of the correlation peak within each of N shift zones. On the other hand, the device also comprises a zero-crossing detector (300) which defines M segments which are limited by the values of the scanning depth for which the speed passes through zero in the set of N zones, a memory (400) storing the values $P_{ij}$ of the correlation peak corresponding to the $i^{th}$ zone ($i=1, \ldots, N$) and the $j^{th}$ segment ($j=1, \ldots, M$), a detector unit (500) reconstructing the speed profile searched by retaining for each segment $j$ the speed profile in the zone $i$ for which $P_{ij}$ is maximum.

2 Claims, 5 Drawing Sheets

|   | $Z_1$ | $Z_2$ | $Z_3$ |
|---|---|---|---|
| $\Delta_1$ |   | × |   |
| $\Delta_2$ |   | × |   |
| $\Delta_3$ | × |   |   |
| $\Delta_4$ | × |   |   |
| $\Delta_5$ | × |   |   |
| $\Delta_6$ |   | × |   |

FIG. 5

DEVICE FOR MEASURING THE SPEED OF MOVING ORGANS AND BLOOD FLOWS BY CORRELATION

The invention relates to a device for measuring the speed of moving organs and blood flows, comprising an intercorrelation circuit which supplies correlation function values on the basis of two successive echographic lines, and a multiplex/interpolation circuit which supplies, on the basis of said correlation function values, an estimate of the speed and the value of the corresponding correlation peak.

The invention is particularly attractively used in the field of echographic examination of moving organs, such as the cardiac walls and blood flows in vessels.

The general technical problem to be solved by any device for measuring the speed of moving organs and blood flows is to obtain an exact as possible estimate of the axial speed of the movement being studied in order to form, using display devices, exact images of organs and blood flows subjected to an ultrasound echographic examination.

In recent years various solutions to this technical problem have been proposed. In this sense French patent application No. 2 590 790 (corresponding to U.S. Pat. No. 4,803,990 assigned to the assignee of the present invention) describes a device for measuring the speed of moving organs and blood flows of the kind set forth which utilises the fact that the ultrasound signals successively backscattered by a moving target are linked by the following equation in the case of recurrent emission with a recurrent period T:

$$S_{n+1}(t) = S_n(t-\tau)$$

This signifies that the signal n+1 is the replica of the preceding signal n, except for a time shift $\tau$. The latter is the supplementary time necessary for the ultrasound wave to travel the path transducer-target-transducer from one emission to an other. In other words:

$$\tau = 2VT/C$$

where V is the speed of the target and C is the speed of sound. It appears that measurement of $\tau$ enables the desired measurement of the speed V.

The intercorrelation function between $S_n(t)$ and $S_{n+1}(t)$ is defined by:

$$C_{n,n+1}(t_o,u) = \int_{t_o}^{t_o + W} S_{n+1}(t + u) S_n(t) dt$$

and verifies that $$C_{n,n+1}(t_o+u) = C_{nn}(t_o, u-\tau)$$

The time to relates to the exploration depth z as to=2z/C.

The function $C_{nn}(t_o,u)$ is an autocorrelation function and, therefore, it is maximum for u=o. Thus, a measure of the time shift, and hence of the speed V, can be obtained by determining for which parameter u the function $C_{n,n+1}(t_o,u)$ is maximum. To this end, the intercorrelation function is sampled with a sampling step $\Delta t$, between $u_{min}=-I\Delta t$ and $u_{max}=I\Delta t$ in steps of 1, in order to obtain 2I+1 correlation function values. The maximum value of these 2I+1 values corresponding to u=uo enables measurement of $\tau$ by using the equality $\tau=u_o$.

In order to remove the errors inherent of sampling during the determination of the maximum value of the correlation function, use can be made of a multiplex/interpolation circuit which supplies, on the basis of correlation function values, a more exact estimate of the speed and the value of the corresponding correlation peak. French patent application No. 2 590 790 discloses an example of such a type of echographic signal processing where the correlation between signals is a correlation which is referred to as a "1 bit" correlation in the sense that the previously used signals $S_{n+1}$ and $S_n$ are reduced to the sign of the ultrasonic signal. It is known that in that case the peak of the correlation function has an isosceles triangular shape. Knowledge of this shape enables reconstruction on the basis of the highest point and its two neighbours, of the complete correlation peak by linear interpolation, thus enabling exact determination of the location of uo.

This known method for measuring speeds, based on analysis of the time shift, offers substantial advantages over other methods which are based, for example on frequency shift or phase shift. It notably enables the use of broadband emission signals, resulting in a good axial measuring resolution. Moreover, taking into account the fact that the method for measurement by correlation does not involve a folding phenomenon, speeds can still be measured beyond the threshold generally imposed by customary instruments.

However, the method disclosed above has the drawback that it may give rise to an error, related to the sampling, in the determination of the position of the correlation peak. Actually, it may occur that the highest point of the sampled correlation function does not belong to the searched correlation peak. This situation can occur when complex fluxes are measured, comprising substantial speed gradients which tend to lower the correlation peak. This error becomes manifest as abrupt discontinuities in the reconstruction of the speed profile V as a function of the scanning depth z.

Thus, the technical problem to be solved in accordance with the invention is to realise a device for measuring the speed of moving organs and blood flows which comprises an intercorrelation circuit which operates with a sampling step $\Delta t$ and which supplies, on the basis of two successive echographic lines shifted by $k\Delta t$ (k=-I, -I+1, . . . , I), 2I+1 correlation function values, and which also comprises a multiplex/interpolation circuit which supplies, on the basis of said correlation function values, an estimate of said speed and the value of the corresponding correlation peak, which device enables unambiguous determination of the position of the maximum of the correlation peak by eliminating the artefacts due to large speed gradients.

The solution to this technical problem in accordance with the present invention consists in that said intercorrelation circuit and multiplex/interpolation circuit supply said estimate of the speed and said value of the correlation peak within each of N zones defined in the time shift interval $[-I\Delta t, +I\Delta t]$, in that it also comprises a zero-crossing detector which defines M segments which are limited by the values of the scanning depth for which the estimate of the speed passes through zero in the set of N zones, a memory storing the accumulated values $P_{ij}$ of the correlation peak corresponding to the $i^{th}$ zone (i=1, . . . , N) and to the $j^{th}$ segment (j=1, ..., M), and in that a detector unit reconstructs the speed profile searched by retaining for each segment j the speed profile in the zone i for which $P_{ij}$ is maximum.

Thus, the invention essentially consists of the "following" of the correlation peak along all possible paths presented by the N zones and the M segments, the selection criterium being the accumulated value of the correlation peak in all patterns. The path retained is that which corresponds to the highest value.

The invention will be described in detail hereinafter with reference to the accompanying diagrammatic drawings.

FIG. 5 shows the structure of the memory used for obtaining the result shown in FIG. 4.

Figure 1:
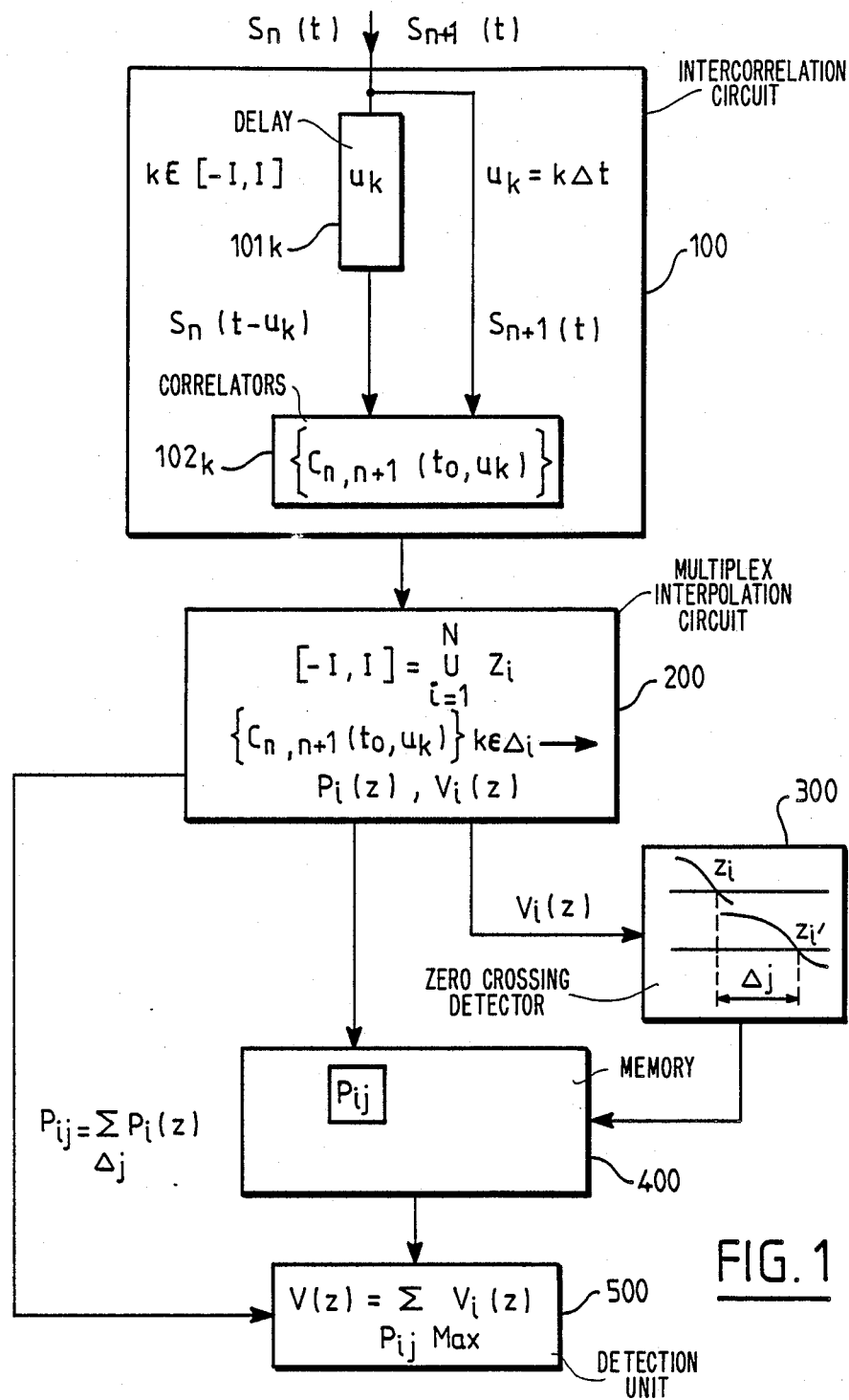
FIG. 1 shows a diagram of the measuring device in accordance with the invention.

FIG. 1 diagrammatically shows a device for measuring the speed of moving organs and blood flows. This device forms part of an apparatus for ultrasonic examination by echography which also comprises (not shown in FIG. 1) at least one ultrasonic transducer which is connected to a stage for the periodical transmission of a pulse signal having a given recurrent frequency F=1/T, and to a stage for receiving echographic signals returned to the transducer and for processing the signals received. French patent application No. 2 590 790 contains a detailed description of these stages. The receiving and processing stage notably comprises a delay line having a recurrent period T which enables the simultaneous reception of two consecutive echographic signals $S_n(t)$ and $S_{n+1}(t)$. As appears from FIG. 1, these two signals $S_n$ and $S_{n+1}$ are processed by an intercorrelation circuit 100 which operates with a sampling step $\Delta t$.

Delay lines $101_k$ shift the signal $S_n(t)$ by an amount $u_k = k\Delta t$, the integer k taking the values $-I, -I+1, \ldots, 1, 0, 1, \ldots, I-1, I$. Subsequently, correlators 102k numbering $2I+1$ supply $2I+1$ correlation function values, i.e.:

$$\{C_{n,n+1}(t_0, u_k)\}_{k\in[-I, I]}.$$

Figure 2:
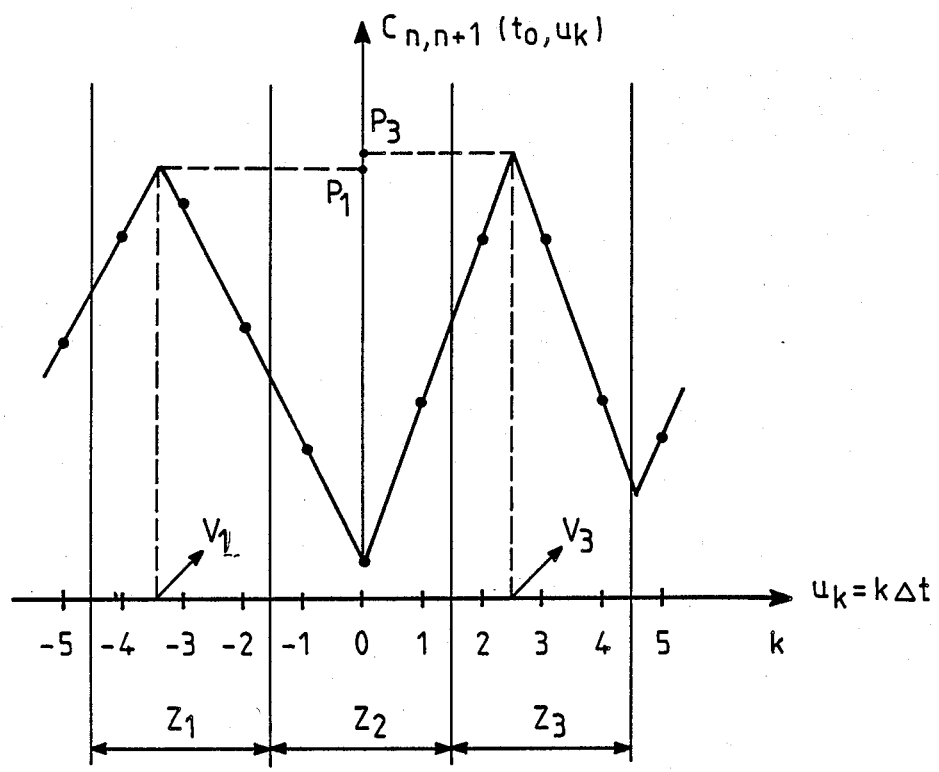
FIG. 2 shows a curve illustrating the correlation function as a function of sampling in the case of a 1-bit correlation, as well as the zone structure.

The correlators 102k may be, for example "1 bit" correlators. FIG. 2 shows the correlation function which, as appears, is in that case formed by correlation peaks having the shape of isosceles triangles. The curve of FIG. 2 corresponds to a value of the number I equal to 5, representing 11 correlation points. This situation occurs, for example, for a transmission frequency of 5 MHz and a sampling frequency of 20 MHz.

The set of $2I+1$ correlation function values supplied by the intercorrelation circuit 100 is subsequently applied to a multiplex/interpolation circuit 200. This circuit 200 parts the correlation points by grouping these points in N zones $Z_i$ (i=1, ..., N). FIG. 2 shows such a partitioning in three zones $Z_1$, $Z_2$ and $Z_3$, each of which comprises three correlation points. Inside each zone $Z_i$ the circuit 200 supplies signals whose values represent an estimate of the speed $V_i$ and of the correlation peak $P_i$. These values being a function of the time to, and hence of the scanning depth, are referenced as $V_i(z)$ and $P_i(z)$. In the case of 1 bit correlation (FIG. 2) $V_i(z)$ and $P_i(z)$ can be calculated by linear interpolation on the highest point of each zone and its two neighbours, the summit of the isosceles triangle thus reconstructed corresponding to the couple $V_i(z)$, $P_i(z)$. This interpolation method is described in the aforementioned French patent application No. 2 590 790.

Figure 3:
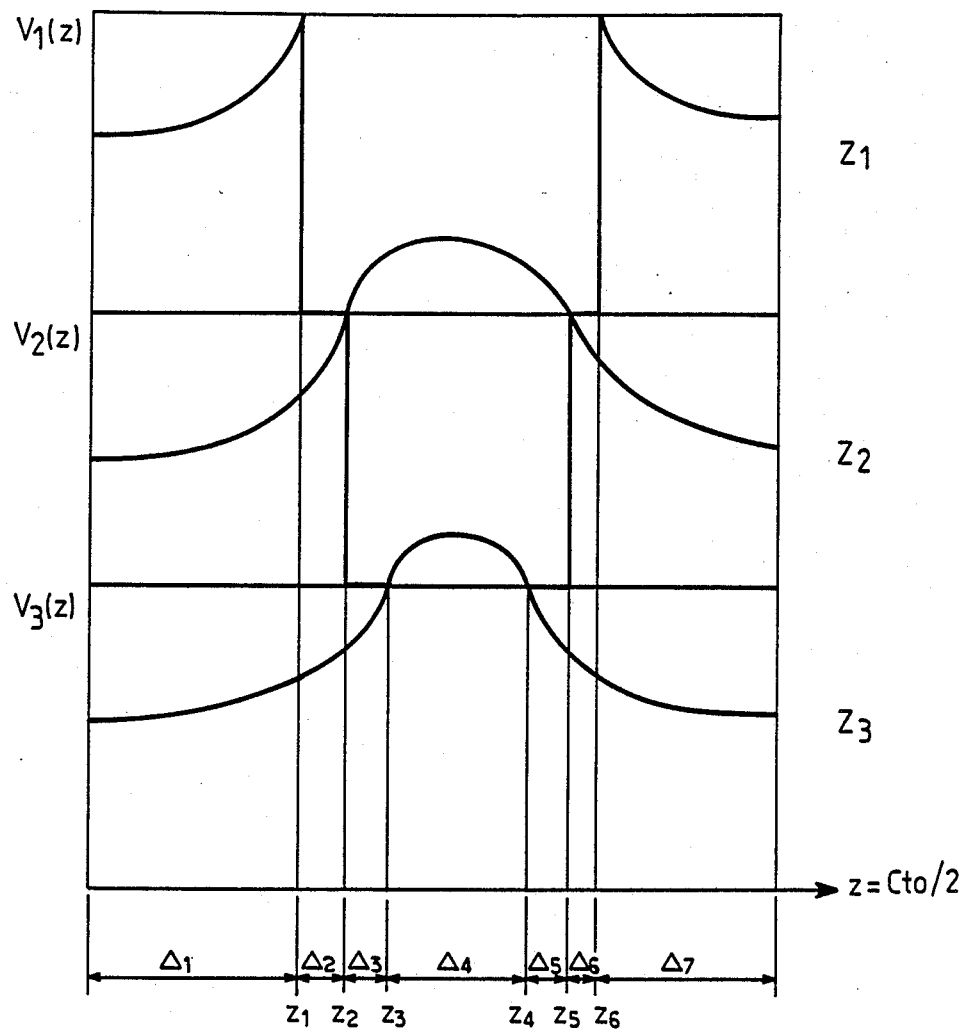
FIG. 3 shows, for each zone, the variations of the estimated speed as a function of the scanning depth, as well as the segment structure.

The N speed profiles $V_i(z)$ can be graphically represented as a function z as appears from FIG. 3. It will be evident from this Figure that the profiles $V_i(z)$ exhibit passages through zero, corresponding to the absence of the correlation peak in the zone $Z_i$ considered for example, for the zone $Z_2$ in FIG. 2. The passages through zero $Z_1, Z_2, \ldots, Z_j, \ldots$ are detected by a zero-crossing detector 300 and enable definition of M segments $\Delta j (j=1, \ldots M)$ along the axis z. In the example shown in FIG. 3, the number of segments $\Delta_1$-$\Delta_j$ is M=7. The M segments $\Delta_j$ thus being defined, within each of these segments for each zone $Z_i$, the values $P_i(z)$ of the correlation peak can be accumulated so as to define a number $P_{ij}$ which can be written as:

$$P_{ij} = \sum_{\Delta j} P_i(z)$$

The N×M values of $P_{ij}$ are stored in a memory 400 which is read by a detection unit 500 as follows: for each segment $\Delta_j$ it is checked for which zone $Z_i$ the parameter $P_{ij}$ is maximum. Thus, the portion of the total profile V(z) searched, within the segment $\Delta_j$, is exactly $V_i(z)$. The values $V_i(z)$ are stored in a memory, reconstruction being realised by successively searching these values until $P_{ij}$ is maximum. This can be translated by the relation:

$$V(z) = \sum_{P_{ij,Max}} V_i(z)$$

Figure 4:
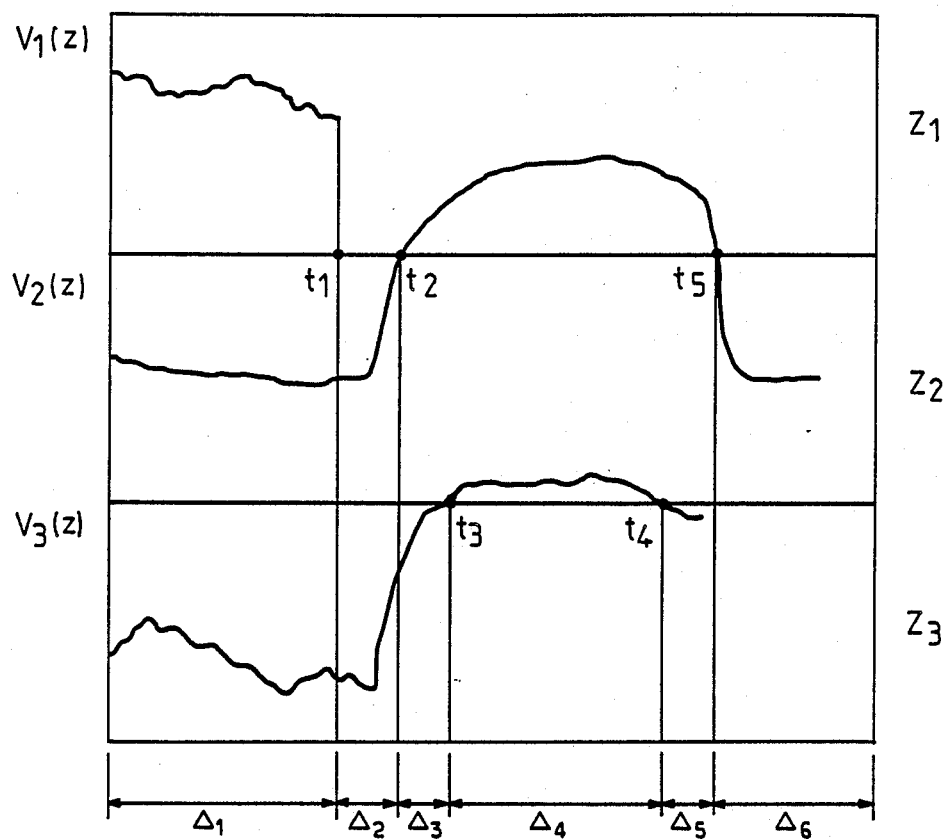
FIG. 4 shows an experimental result obtained by Applicant.

In the example experimentally obtained by Applicant and shown in FIG. 4, the memory 400 had the structure given in FIG. 5. It contained 3×6=18 accumulated values of correlation peaks. The maximum values for each segment $\Delta_j$ are denoted by a cross. The profile V(z) searched is thus given by: $V_2(z)$ for the segments $\Delta_1$, $\Delta_2$, subsequently by $V_1(z)$ for $\Delta_3$, $\Delta_4$, $\Delta_5$ and finally again by $V_2(z)$ for $\Delta_6$.

I claim:

1. In an ultrasonic examination system for measuring the speed of moving organs and blood flows of the type responsive to an echographic signal representing recurrent emission with a recurrent period T comprising intercorrelation means which operates with a sampling step $\Delta t$ which supplies on the basis of two successive echographic lines shifted by $k\Delta t$ (k=$-I, -I+1, \ldots, I$), $2I+1$ correlation function values and multiplex/interpolation means which supplies, on the basis of correlation function values, a signal representing an estimate of the speed and the value manifested by the corresponding correlation peak, the improvement therewith comprising:

said intercorrelation means and multiplex means including means responsive to said echographic signal applied as an input thereto for generating an output signal having first and second values respectively manifesting an estimate of (1) the speed and (2) the value of the correlation peak within each of N zones defined in the time shift interval $\{-I\Delta t, +I\Delta t\}$;

zero crossing detector means responsive to said output signal first value for generating a signal defining M segments limited by the values of the scanning depth for which the estimate of the speed passes through zero in the set of N zones;

memory means responsive to said output signal second value and to the zero crossing detector means generated signal for storing the accumulated values $P_{ij}$ of the correlation peak corresponding to the $i^{th}$ zone ($i=1, \ldots, N$) and to the $j^{th}$ segment ($j=1, \ldots, M$); and detection means responsive to the stored accumulated values $P_{ij}$ for reconstructing the speed profile searched by retaining for each segment j the speed profile in the zone i for which $P_{ij}$ is maximum.

2. A device as claimed in claim 1, characterized in that said intercorrelation means comprises a plurality of 1-bit correlators responsive to said echographic signal for generating a correlation signal and in that said multiplex/interpolation means includes means responsive to said correlation signal for performing linear interpolation in generating said output signal.

* * * * *